United States Defensive Publication [19] (H) [11] T999,003

Ford et al. [43] Oct. 7, 1980

[54] SHIFTED PHOTOGRAPHIC DYES AND COMPOSITIONS, ELEMENTS AND PROCESSES EMPLOYING THEM

[76] Inventors: John A. Ford; Gregory J. Lestina, both of Kodak Park Works, Rochester, N.Y. 14650

[21] Appl. No.: 143,659

[22] Filed: Apr. 25, 1980

Related U.S. Application Data

[62] Division of Ser. No. 949,463, Oct. 10, 1978.

[51] Int. Cl.[3] ..... G03C 5/54; C07C 107/04

[52] U.S. Cl. ..... 430/223; 260/152; 260/192; 260/196; 260/206; 260/156; 260/157; 260/159; 260/165

[57] ABSTRACT

Shifted photographic dyes which have good storage stability, yet rapidly unblock under processing conditions contain a blocked hydroxy group and a neighboring group that anchimerically assists the hydrolytic cleavage of the blocking group under processing conditions.

3 Claims, No Sheets Drawing,

53 Pages Specification

The file of this unexamined application may be inspected and copies thereof may be purchased (849 O.G. 1221, Apr. 9, 1968).